United States Patent [19]

Greczyn

[11] Patent Number: 5,378,452
[45] Date of Patent: Jan. 3, 1995

[54] PROCESS FOR MANUFACTURE OF ANTIPERSPIRANT COSMETIC STICK PRODUCTS

[75] Inventor: Wendy R. Greczyn, Randolph, N.J.

[73] Assignee: Church & Dwight Co., Inc., Princeton, N.J.

[21] Appl. No.: 986,917

[22] Filed: Dec. 8, 1992

[51] Int. Cl.$^6$ .............................................. A61K 7/32
[52] U.S. Cl. ...................................... 424/65; 424/67; 424/68; 424/DIG. 5
[58] Field of Search ................................. 424/65, 68

[56] References Cited

U.S. PATENT DOCUMENTS 4,822,602 4/1989 Sabatelli ................................. 424/65
5,254,332 10/1993 Grezcyn et al. ...................... 424/66

Primary Examiner—José G. Dees
Assistant Examiner—Dwayne C. Jones
Attorney, Agent, or Firm—Charles B. Barris

[57] ABSTRACT

This invention provides an improved process for producing an antiperspirant-deodorant cosmetic stick product. An essential aspect of the process improvement is a phased order of ingredient addition and blending of formulation ingredients under controlled temperature conditions. A bicarbonate salt deodorant is added as the last ingredient during the processing, in order to minimize degradation of the bicarbonate salt under the elevated temperature conditions of the ingredient blending operation.

22 Claims, No Drawings

PROCESS FOR MANUFACTURE OF ANTIPERSPIRANT COSMETIC STICK PRODUCTS

BACKGROUND OF THE INVENTION

Antiperspirants combat axillary odors by inhibiting perspiration through the action of astringent salts such as aluminum and zinc salts, but may be irritating to a large number of users. Deodorants function by neutralizing the objectionable odors resulting from the degradation of several components of perspiration by chemical and microbial action into malodorous fatty acids.

Numerous solid antiperspirant and/or deodorant compositions have been described in the chemical and cosmetic literature. These compositions generally are emulsion sticks or suspensoid sticks. Emulsion sticks contain a solution of the antiperspirant ingredient incorporated into tile stick via an emulsion. Although emulsion sticks are desirable in certain respects, they tend to be unstable, exhibit tackiness, and leave a visible residue on the skin after use. Suspensoid sticks contain the powdered antiperspirant ingredient suspended in the stick without the use of water or an emulsion. While suspensoids have stability, they tend to leave a white chalky residue on the skin after application.

Manufacturers have found that anhydrous antiperspirant stick systems are more marketable and have good consumer acceptance primarily due to the ease of application to the skin, good cosmetic esthetics and an acceptable degree of effectiveness. Previous to the development of anhydrous stick systems, numerous water based systems were developed in which the active astringent salts were solubilized in a thickened or gelled composition. This is exemplified in U.S. Pat. Nos. 2,732,327; 2,857,315; 3,255,082; and 3,928,557. The water based systems are difficult to apply to the skin, and their consistency and effectiveness are variable.

Many anhydrous stick compositions have been described in t]e literature which attempt to improve the delivery and the effectiveness of their antiperspirant and deodorant characteristics. Antiperspirant stick systems consisting of low molecular weight monohydric alcohols in conjunction with polyhydric alcohols are described in U.S. Pat. No. 4,137,306. These sticks have the advantage of quicker drying rates, but the residue of the polyhydric alcohols in combination with the astringent salts produces a high degree of tack, and their effectiveness is limited to the type and amount of astringent salts that could be incorporated in the stick matrix.

Anhydrous stick compositions that suspend the aluminum salt in a hydrophobic matrix are described in U.S. Pat. No. 4,049,792. These compositions employ waxy materials and long chain fatty esters to form a stick that delivers the active astringent salts to the skin. Cosmetic stick compositions made in accordance with these embodiments are greasy, and the active astringent salt is enveloped in a manner that prevents maximum performance. To alleviate this inherent negative characteristic, volatile silicone fluids replacement of the less volatile long chain fatty esters is described in U.S. Pat. No. 4,126,679. This disclosure teaches the advantage of utilizing a volatile non-staining liquid such as cyclic dimethylpolysiloxanes (referred to as volatile silicones), in combination with various types of waxes, as a carrier for the active astringent salts in an antiperspirant stick composition. Similar antiperspirant stick compositions containing volatile silicones are described in U.S. Pat. Nos. 4,511,554; 4,980,156; and 4,985,238.

With respect to deodorant activity, sodium bicarbonate has long been recognized for its deodorant properties, and has commonly been used as a household deodorant. Plain powdered sodium bicarbonate, or sodium bicarbomate diluted with talc or other filler, has been used as an underarm deodorant as disclosed in U.S. Pat. No. 4,382,079. Other publications which describe cosmetic stick compositions containing a bicarbonate deodorant include U.S. Pat. Nos. 4,822,602 and 4,832,945.

However, the development of a practical and effective antiperspirant composition in cosmetic stick form which is also capable of deodorization, and which is capable of consumer acceptability, presents many factors which are unique. Because sodium and potassium bicarbonate have only limited solubility in water, alcohol and other solvents, the preparation of a composition suitable for dispensing in cosmetic stick form has involved many processing obstacles. In addition to the problem of limited solubility, sodium bicarbonate is incompatible with the active astringent salts and with other ingredients of conventional stick compositions. Also, the dimensional stability of the cosmetic stick containing sodium bicarbonate, and the esthetic appearance and the "feel" on the skin, are just a few of the additional difficulties encountered in the preparation of a low residue antiperspirant-deodorant cosmetic stick product.

Another significant problem associated with the incorporation of a bicarbonate deodorant ingredient in an antiperspirant formulation is the tendency for chemical interaction of the basic bicarbonate salt with acidic ingredients during processing. Also, under the elevated temperature conditions required for the admixing and blending of ingredients, bicarbonate degradation and evolution of carbon dioxide occur.

There is continuing interest in the development of antiperspirant cosmetic stick products which exhibit deodorizing activity, and in improved processes for their preparation.

Accordingly, it is an object of this invention to provide an antiperspirant cosmetic stick product containing an ingredient which has deodorant properties.

It is another object of this invention to provide an improved process for the manufacture of an antiperspirant-deodorant cosmetic stick product which contains a bicarbonate deodorant ingredient, and which is characterized by excellent esthetics and cosmetic properties.

Other objects and advantages of the present invention shall become apparent from the accompanying description and example.

DESCRIPTION OF THE INVENTION

One or more objects of the present invention have been accomplished by the provision of a process for preparing an antiperspirant-deodorant cosmetic stick product which comprises (1) heating between about 10–50 parts by weight of a volatile silicone oil ingredient to a temperature of about 120°–220° F.; (2) adding to the heated silicone oil ingredient between about 1–30 parts by weight of a liquid emollient ingredient, between about 12–24 parts by weight of a low melting point wax ingredient, between about 0.5–15 parts by weight of a compatibility enhancing ingredient, and between about 0.5–5 parts by weight of a surfactant ingredient to form a homogeneous fluid medium; (3)

adding between about 18-30 parts by weight of an antiperspirant ingredient to the heated fluid medium; (4) adding between about 0.05-30 parts by weight of a particulate alkali metal bicarbonate deodorant ingredient to about 10-30 parts by weight of volatile silicone oil ingredient to form a separate homogeneous fluid suspension medium; (5) passing individual streams of heated fluid medium and bicarbonate suspension medium into a mixing zone to form a heated liquid blend, and dispensing the fluid blend into cosmetic stick containers; and (6) cooling the container contents to form solid sticks at room temperature.

An invention antiperspirant deodorant cosmetic stick product typically contains the following weight proportions of main ingredients:

| Ingredient | Weight |
|---|---|
| volatile silicone oil | 25-50 |
| liquid emollient | 2-20 |
| wax (MP 95°-180° F.) | 15-20 |
| antiperspirant | 20-28 |
| bicarbonate deodorant | 0.1-25 |
| compatibility enhancer | 1-10 |
| surfactant | 1-3 |

The volatile silicone oil ingredient in an antiperspirant-deodorant cosmetic stick product of the present invention preferably is a cyclic or linear polydimethyliloxane containing between about 3-9 silicon atoms. A suitable cyclic volatile polydimethylsiloxane compound is illustrated by the formula:

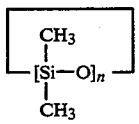

where n is an integer with a value of about 3-7.

A suitable linear polydimethylsiloxane is illustrated by time formula:

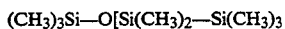

where n is an integer with a value of about 1-7.

Linear volatile silicone compounds generally have viscosities of less than about 5 centistokes at 25° C., while the cyclic type compounds have viscosities of less than about 10 centistokes.

Typical of the volatile silicone compounds that can be employed for purposes of the present invention is cyclomethicone, which is a cyclic dimethylpolysiloxane conforming to the above formula where n averages between 3-6. Dow Corning 245 Fluid (Dow Corning) is a cyclic volatile silicone which is commercially available. *CTFA Cosmetic Ingredient Dictionary*, Third Edition, (Estrin et al., Editors; The Cosmetic, Toiletry and Fragrance Association, Inc.; 1982) lists cyclic silicones on page 60, under the entry "Cyclomethicone".

The liquid emollient ingredient of an invention cosmetic stick product is selected from one or more water-insoluble organic compounds which are liquid at 25° C. and which contribute a combination of properties that are advantageous in an invention antiperspirant-deodorant cosmetic stick product.

The term "water-insoluble" as employed herein refers to an emollient ingredient which has a water-solubility of less than about one weight percent at 25° C.

A present invention emollient ingredient exhibits a low degree of irritation and toxicity in topical application]s, and provides a softening or soothing effect on surface skin tissue.

Preferred water-insoluble liquid emollients include fatty acids such as oleic and ricinoleic; fatty alcohols such as oleyl, lauryl and hexadecyl; esters such as diisopropyl adipate, benzoic acid esters: of $C_9$-$C_{15}$ alcohols, and isononyl isononanoate; alkanes such as mineral oil; silicones such as dimethylpolysiloxane and cyclic dimethylpolysiloxane; and ethers such as polyoxypropylene butyl ether and polyoxypropylene cetyl ether. Preferred water-insoluble liquid emollients include diisopropyl adipate, 2-ethylhexyl palmitate, dimethylpolysiloxane (50 cst.), and polyoxypropylene (14) butyl ether.

The low melting point wax ingredient of a present invention cosmetic stick product comprises one or more organic compounds which have a melting point in the range between about 95°-180° F.

Suitable types of wax-like compounds include fatty acids, fatty alcohols, fatty acid esters, fatty acid amides, and the like, which have an aliphatic chain length between about 8-30 carbon atoms. Illustrative of wax-like compounds are cetyl alcohol, palmitic acid, myristyl alcohol, stearyl alcohol, paraffin, and the like, and mixtures thereof.

The low melting point wax ingredient can include up to about 30 weight percent, based on the weight of wax ingredient, of a wax which has a melting point between about 180°-220° F. Illustrative of these higher melting waxes are beeswax, spermaceti, carnauba, bayberry, candelilla, monta, ozokerite, ceresin, paraffin, castor wax, Fischer-Tropsch waxes, and the like.

The antiperspirant ingredient of a present invention cosmetic stick product typically is a particulate astringent compound which has an average particle size between about 1-100 microns. Superior cosmetic stick properties are obtained if part or all of the antiperspirant ingredient is in the form of particles which have a diameter less than about one micron.

Suitable astringent compounds include aluminum chloride, aluminum chlorohydrate, aluminum sulfocarbolate, aluminum sulfate, aluminum-zirconium chlorohydrate, zinc sulfate, zinc sulfocarbolate, and zirconium chlorohydrate. Preferred types of astringent compound are aluminum chlorohydrates and aluminum-zirconium chlorohydrates, such as aluminum zirconium tetrachlorohydrex glycine which is commercially available as Rezal 36 GP Superultrafine (Reheis).

The bicarbonate deodorant ingredient of an invention cosmetic stick product is selected from alkali metal and ammonium bicarbonates, such as sodium bicarbonate, potassium bicarbonate, and ammonium bicarbonate, and mixtures thereof. The bicarbonate deodorant ingredient can contain up to about 30 weight percent, based on the weight of deodorant ingredient, of an alkali metal or ammonium carbonate compound.

The average particle size of the bicarbonate deodorant ingredient can be in the range between about 1-00 microns. Improved cosmetic stick properties are obtained if part or all of the bicarbonate ingredient has a particle size diameter less than about one micron. Colloidal size particles facilitate incorporation into the cosmetic stick matrix, and the resultant stick composition has a smoother no-gritty feel when applied to the skin.

The compatibility enhancing ingredient of an invention cosmetic stick product is selected from organic compounds and polymers which enhance the homogeneous blending of the organic and inorganic ingredients which form the cosmetic stick matrix.

Suitable compatibility enhancing organic compounds and polymers include $C_6-C_{22}$ fatty alcohols and their ethoxylated and propoxylated ether derivatives, gum arabic, gum karaya, gum tragacanth, guar gum, locust bean gum, xanthan gum, carrageenan, alginate salt, casein, dextran, pectin, agar, 2-hydroxyethyl starch, 2-aminoethyl starch, 2-hydroxyethyl cellulose, methyl cellulose, carboxymethyl cellulose salt, cellulose sulfate bi-salt, polyacrylamide, methyl vinyl ether/maleic anhydride copolymer, styrene/maleic anhydride copolymer, ethylene/maleic anhydride copolymer, and the like.

Propylene glycol butyl ether is commercially available as PPG-14 butyl ether (Fluid AP). Sodium carboxymethylcellulose (CMC) is available in powder or granular form (50–200 microns), and with a degree of substitution (DS) range of 0.38–1.4.

The polyalkylene glycol ethers of $C_4-C_{22}$ alcohols preferably have a Hydrophile-Lipophile Balance value (HLB) of about 8–15.

The surfactant ingredient of an invention cosmetic stick product is selected from nonionic, cationic and anionic polymers.

Suitable surfactant polymers include cetyltrimethylammonium bromide; sodium lauryl sulfate; sodium dodecylbenzenesulfonate; ammonium lignosulfonate; condensation products of ethylene oxide with fatty alcohols, amines or alkylphenols; partial esters of fatty acids and hexitol anhydrides; polyalkylene glycol esters; and the like. Illustrative of a preferred type of surfactant polymer is polyethylene glycol (PEG) stearate, which is commercially available as PEG 600 distearate.

Optional ingredients also may be included in an invention cosmetic stick formulation, such as bacteriostats, fungistats, fillers, stabilizing agents, antioxidants, pigments, coloring agents, perfumes, hardeners, chelating agents, and the like.

A bacterostat such as 2,4,4'-trichloro-2'-hydroxydiphenyl ether (Triclosan) typically is added in a quantity between about 0.08–3 weight percent, based on the weight of the cosmetic stick product.

An optional ingredient such as colloidal silica suspending agent is added in a quantity between about 1–3 weight percent, based on the weight of the cosmetic stick product.

A present invention cosmetic stick product preferably has a hardness penetration value between about 4–12 millimeters, as determined by American Society For Testing Materials (ASTM) Method D5.

A present invention antiperspirant-deodorant cosmetic stick product has exceptional properties for treating or preventing perspiration and malodor associated with human underarm perspiration. A present invention cosmetic stick product can be applied effectively with safety and comfort for reduction of underarm perspiration and offensive odors.

The practice of the invention process for the production of a cosmetic stick product can be conducted in conventional equipment, and is readily adaptable to a commercial-scale manufacturing operation.

One essential aspect of the present invention process is a phased order of ingredient addition and blending under controlled temperature conditions. Another essential aspect of the invention process is a short time lapse between the alkali metal bicarbonate deodorant ingredient addition and mixing step at the point-of-fill site, and the cosmetic stick container filling and solidifying step.

Adding the bicarbonate deodorant as the last ingredient of the blended formulation, and processing the formulation to the solid cosmetic stick formation stage within a short time period, are factors which minimize the degradation of the bicarbonate ingredient, and the undesirable formation of water and carbon dioxide vapor byproducts. The addition and mixing of the bicarbonate deodorant ingredient into the formulation, and the dispensing of the formulation into cosmetic stick containers, can be accomplished as an essentially instantaneous procedure by utilizing an integrated mixing valve nozzle device, such as the type described in U.S. Pat. No. 2,816,518; 3,454,198; 3,949,904; 4,318,429; 4,549,813; 5,046,538; 5,094,276; and the like.

The following example is further illustrative of the present invention. The components and specific ingredients are presented as being typical, and various modifications can be derived in view of the foregoing disclosure within the scope of the invention.

EXAMPLE

This example illustrates a pilot-plant procedure for the preparation of an antiperspirant-deodorant cosmetic stick product in accordance with the present invention.

A stainless tank is provided which is equipped with turbine agitation.

Silicone oil DC 245 (600 lbs, Dow Corning) is charged to the mixing tank. Agitation (55–65 RPM) is initiated, and heating the liquid medium to 176° F. is commenced.

During the heating period, the following order of ingredients are added to the stirred liquid medium:

|  | lbs. |
|---|---|
| diisopropyl adipate | 60 |
| PPG 14 butyl ether (Americol) | 40 |
| stearyl alcohol | 340 |
| castor wax (MP-70) | 60 |
| eicosanol | 10 |
| PEG 600 distearate (Mazer) | 40 |

The mixture is stirred at 176° F. for about 30 minutes until the ingredients are melted and the liquid medium is homogeneous. The stirring speed is reduced to about 35 RPM, then Cab-o-sil M-5 (15 lbs, Cabot) and aluminum zirconium tetrachlorohydrex glycine (480 lbs, Rebels) are added. The temperature is maintained at 176° F. for about 40 minutes until the fluid medium is uniform, and then the temperature is lowered to 124° F.

Sodium bicarbonate 3 DF (140 lbs, Church & Dwight) and a fragrance (6 lbs, 1FF 567-AT) respectively are added with stirring to Silicone oil DC 245 (245 lbs, Dow Corning) in a second mixing tank at a temperature of 124° F. to form a homogeneous suspension medium.

The contents of the two mixing tanks which contain heated fluid medium are transferred to separate fill tanks through a Greer mill, and the fill tanks are connected to a mixing and dispensing nozzle device, of the type described in U.S. Pat. No. 5,094,276. The nozzle device is adapted for homogeneously blending the two separate streams of fluid media, and dispensing a predetermined quantity of the blended fluid.

Plastek 2 oz. bottom-fill stick containers are filled with the blended fluid. The container contents are cooled to a room temperature solid stick over a period of about 45 minutes. The average hardness value of the solid sticks is 7 (ASTM Method D5).

What is claimed is:

1. A process for preparing an antiperspirant-deodorant cosmetic stick product which comprises (1) heating between about 10–50 parts by weight of a volatile silicone oil ingredient to a temperature of about 120°–220° F.; (2) adding to the heated silicone oil ingredient between about 1–30 parts by weight of a liquid emollient ingredient, between about 12–24 parts by weight of a low melting point wax ingredient, between about 0.5–15 parts by weight of a compatibility enhancing ingredient, and between about 0.5–5 parts by weight of a surfactant ingredient to form a homogeneous fluid medium; (3) adding between about 18–30 parts by weight of an antiperspirant ingredient to the heated fluid medium; (4) adding between about 0.05–30 parts by weight of a particulate alkali metal bicarbonate deodorant ingredient to about 10–30 parts by weight of volatile silicone oil ingredient to form a separate homogeneous fluid suspension medium; (5) passing individual streams of heated fluid medium and bicarbonate suspension medium through an integrated mixing valve nozzle device to form a heated fluid blend, and to dispense the fluid blend into cosmetic stick containers; and (6) cooling the container contents to form solid sticks at room temperature.

2. A process in accordance with claim 1 wherein the volatile silicone oil ingredient comprises between about 25–50 weight percent of the cosmetic stick product.

3. A process in accordance with claim 1 wherein the volatile silicone oil ingredient comprises a cyclic or linear polydimethylsiloxane containing 3–9 silicon atoms.

4. A process in accordance with claim 1 wherein the liquid emollient ingredient comprises between about 2–20 weight percent of the cosmetic stick product.

5. A process in accordance with claim 1 wherein the liquid emollient ingredient is a water-insoluble organic acid, ester or ether compound.

6. A process in accordance with claim 1 wherein the liquid emollient ingredient is diisopropyl adipate.

7. A process in accordance with claim 1 wherein the wax ingredient has a melting point in the range of about 95°–180 °F., and comprises between about 15–20 weight percent of the cosmetic stick product.

8. A process in accordance with claim 1 wherein the wax ingredient is selected from $C_8$–$C_{30}$ alcohol, acid, ester and amide compounds.

9. A process in accordance with claim 1 wherein the wax ingredient comprises stearyl alcohol or castor wax or a mixture thereof.

10. A process in accordance with claim 1 wherein the compatibility enhancing ingredient comprises between about 1–10 weight percent of the cosmetic stick product.

11. A process in accordance with claim 1 wherein the compatibility enhancing ingredient is selected from polyalkylene glycol ethers of $C_4$–$C_{22}$ alcohols, and has an HLB value between about 8–15.

12. A process in accordance with claim 1 wherein the compatibility enhancing ingredient is polypropylene glycol butyl ether.

13. A process in accordance with claim 1 wherein the surfactant ingredient comprises between about 1–3 weight percent of the cosmetic stick product.

14. A process in accordance with claim 1 wherein the surfactant ingredient is selected from nonionic, cationic and anionic polymers.

15. A process in accordance with claim 1 wherein the surfactant ingredient is polyalkylene glycol diester.

16. A process in accordance with claim 1 wherein the antiperspirant ingredient comprises between about 20–28 weight percent of the cosmetic stick product, and is a particulate solid having an average particle size between about 1–100 microns.

17. A process in accordance with claim 1 wherein the antiperspirant ingredient is selected from astringent aluminum and zirconium compounds, and complexes or mixtures thereof.

18. A process in accordance with claim 1 wherein the antiperspirant ingredient is an aluminum-zirconium tetrachlorohydrate compound.

19. A process in accordance with claim 1 wherein the deodorant ingredient comprises between about 0.1–25 weight percent of the cosmetic stick product, and is a particulate solid having an average particle size between about 1–100 microns.

20. A process in accordance with claim 1 wherein the deodorant ingredient is sodium or potassium bicarbonate or a mixture thereof.

21. A process in accordance with claim 1 wherein the deodorant ingredient is alkali metal bicarbonate containing up to about 30 weight percent of alkali metal carbonate, based on the weight of deodorant ingredient.

22. A process in accordance with claim 1 wherein between about 0.08–3 weight percent of a bacteriostat is included as an additional ingredient, based on the weight of cosmetic stick product.

* * * * *